United States Patent
Forkey et al.

(10) Patent No.: US 7,699,773 B2
(45) Date of Patent: Apr. 20, 2010

(54) REPAIRABLE ENDOSCOPE

(75) Inventors: Richard E. Forkey, Westminster, MA (US); William P. Barnes, Acton, MA (US); Robert N. Ross, Gardner, MA (US); Joseph N. Forkey, Princeton, MA (US)

(73) Assignee: Precision Optics Corporation, Gardner, MA (US)

( * ) Notice: Subject to any disclaimer, the term of this patent is extended or adjusted under 35 U.S.C. 154(b) by 1056 days.

(21) Appl. No.: 11/161,934

(22) Filed: Aug. 23, 2005

(65) Prior Publication Data
US 2006/0276691 A1    Dec. 7, 2006

(51) Int. Cl.
*A61B 1/06* (2006.01)
(52) U.S. Cl. .................... 600/172; 600/133; 600/136; 600/138; 600/140; 600/176
(58) Field of Classification Search ......... 600/127–130, 600/133
See application file for complete search history.

(56) References Cited

U.S. PATENT DOCUMENTS

| | | | |
|---|---|---|---|
| 4,036,218 A | 7/1977 | Yamashita et al. | 128/4 |
| 4,148,550 A * | 4/1979 | MacAnally | 359/435 |
| 4,416,268 A | 11/1983 | Hagino | 128/6 |
| 4,895,138 A | 1/1990 | Yabe | 128/6 |
| 4,905,082 A | 2/1990 | Nishigaki et al. | 358/98 |
| 5,051,824 A | 9/1991 | Nishigaki | 358/98 |
| 5,156,142 A | 10/1992 | Anapliotis et al. | 128/6 |
| 5,359,453 A * | 10/1994 | Ning | 359/435 |
| 5,419,313 A * | 5/1995 | Lemke | 600/133 |
| 5,456,245 A * | 10/1995 | Bornhop et al. | 600/139 |
| 5,569,163 A * | 10/1996 | Francis et al. | 600/133 |
| 5,599,278 A * | 2/1997 | Hibbard | 600/133 |
| 5,601,525 A | 2/1997 | Okada | |
| 5,842,972 A * | 12/1998 | Wulfsberg | 600/167 |
| 5,954,637 A * | 9/1999 | Francis | 600/138 |
| 5,984,861 A | 11/1999 | Crowley | 600/175 |
| 6,095,970 A | 8/2000 | Hidaka et al. | 600/110 |
| 6,364,831 B1 | 4/2002 | Crowley | 600/175 |
| 6,419,628 B1 | 7/2002 | Rudischhauser | |
| 6,425,857 B1 * | 7/2002 | Rudischhauser et al. | 600/112 |
| 6,503,196 B1 * | 1/2003 | Kehr et al. | 600/176 |
| 6,547,722 B1 * | 4/2003 | Higuma et al. | 600/133 |
| 6,565,505 B2 * | 5/2003 | Ishibiki | 600/133 |

(Continued)

FOREIGN PATENT DOCUMENTS

DE    197 13 275 A1    10/1998

(Continued)

OTHER PUBLICATIONS

Henke, Sass, Wolf- Mini-Rigid Borescopes, Specification Sheet.

*Primary Examiner*—Matthew J Kasztejna

(57) ABSTRACT

A rigid endoscope includes an outer housing subassembly that supports an optics subassembly. The outer housing subassembly includes concentric tubes with optical fiber for providing object illumination. The optics subassembly includes a tubular sheath sealed at both ends for carrying lenses and other optical elements. A slow-curing adhesive material fills an annular gap between the optics and outer housing subassemblies. The adhesive material has a tear strength that seals and positions the optics subassembly for normal use and that enables the optics subassembly to be withdrawn from the outer housing subassembly for repair.

12 Claims, 9 Drawing Sheets

U.S. PATENT DOCUMENTS

| | | |
|---|---|---|
| 6,569,087 B2 | 5/2003 | Naito et al. .................. 600/156 |
| 6,589,165 B2 | 7/2003 | Bodor et al. ................. 600/172 |
| 2003/0191366 A1 | 10/2003 | Ishibiki ...................... 600/133 |
| 2004/0176662 A1 | 9/2004 | Forkey |
| 2005/0182299 A1* | 8/2005 | D'Amelio et al. ........... 600/175 |

FOREIGN PATENT DOCUMENTS

| | | |
|---|---|---|
| EP | 0 044 018 A1 | 1/1982 |
| JP | 62-066220 | 3/1987 |
| JP | 05-154102 | 8/1993 |
| WO | 2004036266 A2 | 4/2004 |

\* cited by examiner

REPAIRABLE ENDOSCOPE

CROSS REFERENCE TO RELATED APPLICATION

This application incorporates by reference U.S. patent application Ser. No. 10/383,236 to Forkey et al. filed Mar. 6, 2003, now U.S. Pat. No. 6,955,644 granted Oct. 8, 2005 for an Autoclavable Endoscope, assigned to the same assignee as the present application.

FIELD OF THE INVENTION

This invention relates to endoscopes adapted for repair and more particularly to autoclavable endoscopes adapted for repair.

DESCRIPTION OF RELATED ART

Endoscopes come in two basic forms. In one form the endoscope is flexible. Optical fibers transfer an image from an optical objective to an eyepiece or other viewing device. The fibers produce image pixels of the image from the optical objective. Endoscopes of the second form are called rigid endoscopes. This invention is particularly applicable to rigid endoscopes. A rigid endoscope includes a tubular structure that carries an optical objective at a distal end and a relay lens system that transfers the image to a viewing device or eyepiece at a proximal end. Such devices typically provide better spatial resolution than flexible endoscopes do.

Rigid endoscopes are used in various surgical and diagnostic medical procedures, so it is important that devices be capable of being sterilized. There are different ways to sterilize medical instruments. However, autoclaving is a preferred process. During this process, an endoscope is placed in an autoclave, and steam is introduced to gradually raise the temperature to about 270° F. This temperature is maintained for some interval and then reduced in a controlled manner.

During this process, temperature differentials exist throughout the endoscope. Endoscopes, particularly rigid endoscopes, typically comprise materials characterized by different thermal coefficients of expansion. Consequently, during the autoclaving process it is possible for an endoscope to be subjected to different mechanical stresses. Experience has shown that repeated autoclaving of rigid endoscopes can damage seals whereupon steam can enter the endoscope with resultant condensation in the optical path distorting or degrading the quality of the image. Endoscopes are also subject to other stresses during normal use. Sometimes they are dropped or accidentally struck against some object during normal use.

Should any of these or a number of other events occur, damage can result to the endoscope. Many endoscopes are integral assemblies, so they can not be repaired. Replacing, rather than repairing, a damaged endoscope is very expensive. So some attempts have been made to facilitate repair by producing endoscopes as assemblies of two or more modules that can be separated. With this approach, only the damaged module needs to be replaced.

For example, U.S. Pat. No. 4,416,268 (1983) to Hagino discloses an endoscope. An endoscope body has a control section at a proximal end. A first armored tube conveys a light guide to the control section; a second armored tube carries an air feed tube, water feed tube, suction tube and conductor. The first and second armored tubes are detachable from the endoscope control body, so a repair can be made by replacing the tubes without replacing the control section and an insert section that extends distally from the control section.

U.S. Pat. No. 5,156,142 (1992) to Anapliotis et al. discloses an arthroscope with a shaft that carries an optical unit as part of an observation component and an illumination component. The illumination component includes a double-walled sheath that forms an annulus for carrying optical fibers and that forms a central passage. The observation component includes a lens formed with various channels about the periphery within a guidance tube to fit within the passage formed by the illumination component. As a result, the observation component can be removed from the arthroscope for repair.

An endoscope disclosed in U.S. Pat. No. 6,569,087 (2003) to Nalto et al. facilitates repair by providing a separable water supply connector. Repairs to the conduits for the water supply can then be made expeditiously without the need for replacing the endoscope.

U.S. Pat. No. 6,589,165 (2003) to Bodor et al. describes an endoscope with a modular structure. The endoscope is characterized by having interchangeable image transmission systems. Should the optical components in the image transmission system fail, a mechanical latch is released. The damaged image transmission system can be removed from endoscope for independent repair or replacement.

Endoscopes embodying the disclosure in U.S. Patent Publication No. US 2004-0176662 of Forkey et al. are characterized by including an inner optics assembly that is constructed with a tubular sheath that contains optical elements and is sealed at both ends to withstand the rigors of autoclaving. With this construction the tubular sheath attaches at the distal end to an inner tube of an outer housing subassembly by an epoxy seal. Epoxy seals form strong bonds that are not readily broken except under a carefully controlled environment.

If damage occurs to the optics of the Hagino, Anapliotis or Nalto et al. endoscopes, it becomes necessary to ship such an endoscope back to the factory or repair facility with a capability of breaking brazed joints to allow separation of the endoscope into its constituent components. Although the Bodor et al. patent suggests the use of interchangeable image transmission units, there is no disclosure of the exact structure and process for achieving that result except by reference to "interlocking" and a "mechanical latch" which are not readily ascertained by the disclosure. Further, it appears that in the Bodor et al. there is a sealing window across the distal end of an outer tube. Forkey et al. disclose a construction whereby a sealed optical subassembly can be released from an outer housing assembly by breaking an epoxy seal. This approach, however, still requires repairs at a qualified repair facility.

What is needed is an endoscope with a construction that allows the simple and safe removal and/or exchange of an optics subassembly from an endoscope at a factory or repair facility. What is also needed is such an autoclavable endoscope that could allow qualified personnel to exchange optics subassemblies within an endoscope at a user's site.

SUMMARY

Therefore it is an object of this invention to provide an endoscope that is easy to repair.

Another object of this invention is to provide an endoscope that is easy to repair and that can withstand the rigors of repeated autoclaving.

Still another object of this invention is to provide an endoscope that is easy to manufacture, facilitates necessary adjustments during manufacture and is readily disassembled and reassembled during repair.

In accordance with this invention an endoscope subject to a variety of forces in normal use comprises an optics subassembly and an outer housing subassembly. The optics subassembly includes an external sheath. The outer housing subassembly includes a passage therethrough whereby a gap exists between optics and outer housing subassemblies. An adhesive material fills at least a portion of the gap for contacting said subassemblies thereby preventing displacement therebetween during normal use. The material has a tear strength that permits the separation of the subassemblies for repair.

In accordance with another aspect of this invention, an autoclavable endoscope has distal and proximal ends and comprises outer housing and optics subassemblies. The outer housing subassembly has a central lumen therethrough. The optics subassembly includes a tubular sheath extending through the central lumen and having sealed windows at each of the distal and proximal ends. A plurality of optical elements in the tubular sheath forming an image of an object and presenting the image for viewing. A material intermediate the outer housing and the tubular sheath prevents displacement therebetween during normal use. The material has a tear strength that permits the separation of the optics subassembly from the outer housing subassembly.

In accordance with yet another aspect of this invention, a repairable, autoclavable endoscope comprises an optics subassembly, an outer housing subassembly, an eyecup and adhesive material. The optics subassembly includes a sheath having a predetermined cross section extending proximally from a distal end. A proximal collar attaches to the proximal end of the external sheath. Optical elements are carried in the sheath and collar for presenting an image at the proximal end of the optics subassembly representing an object proximate the distal end of the optics subassembly. A position stabilizer at the proximal end of the collar establishes the axial position of the optics subassembly in the endoscope. The outer housing subassembly, that includes a body portion and an outer sheath attached to the body portion, has a passage therethrough. The passage terminates at an open distal end for receiving the optics subassembly. The body portion includes a structure for engaging the position stabilizer thereby to define the position of the optics subassembly. The eyecup attaches to the proximal end of the body portion for applying an axial force to the position stabilizer thereby to fix the position of the optics subassembly with respect to the outer housing subassembly. The adhesive material lies between the sheath and the outer sheath over a portion extending proximally from the distal end. The adhesive material has a tear strength that permits the separation of the subassemblies for repair.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
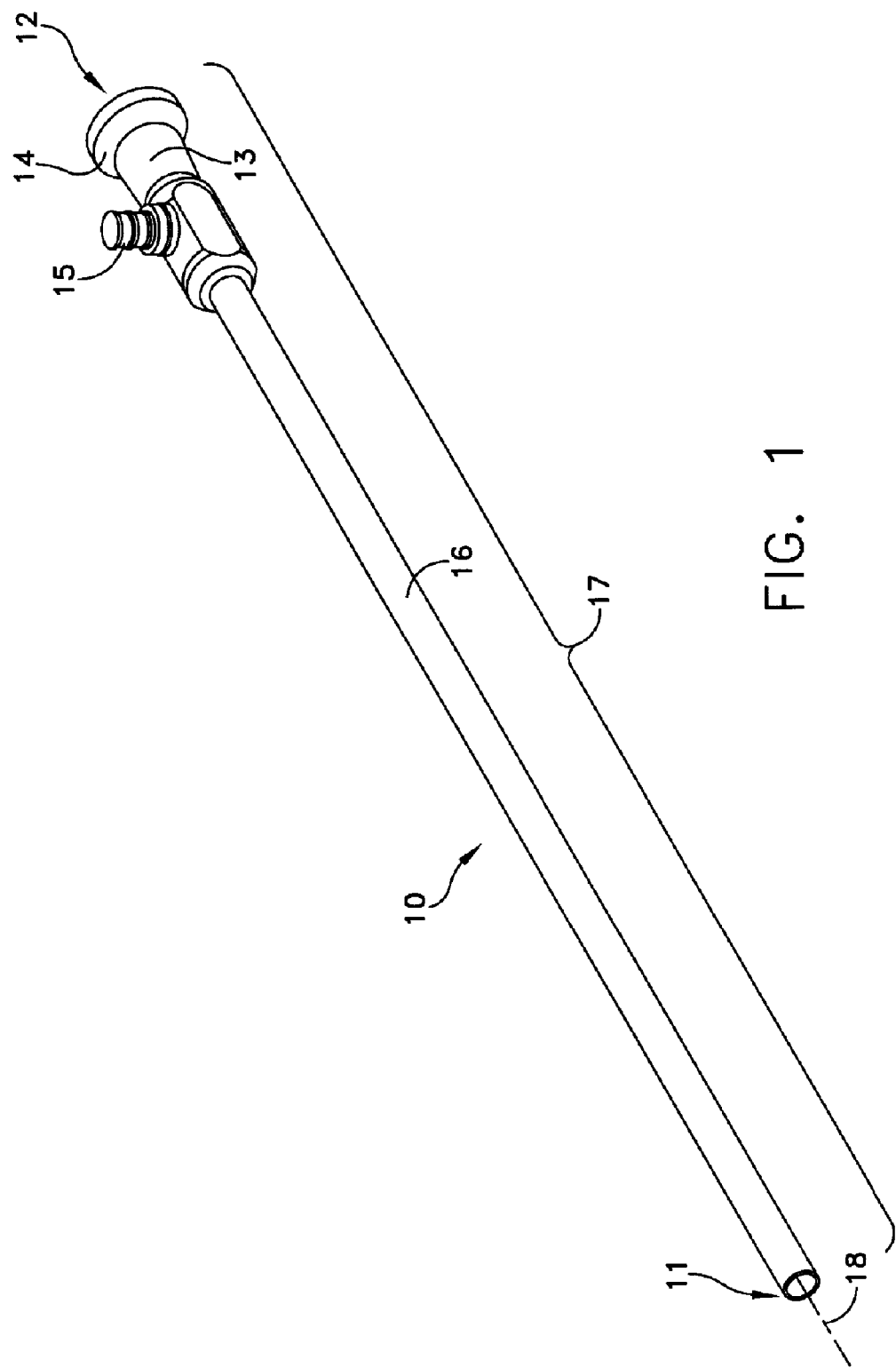
FIG. 1 is a perspective view of one embodiment of an endoscope constructed in accordance with this invention.

FIG. 1 depicts an endoscope 10 as it appears to medical personnel for use. It extends between a distal end 11, the end closest to the object to be imaged, and a proximal end 12, the end closest to the person using the device. This view depicts an optical body 13 with an eyecup 14 through which the image is viewed. A fiber post 15 receives an output connection from an illumination source thereby to provide light for transmission through optical fiber to illuminate the object being imaged. An outer sheath of a tube 16 extends from the optical body. All of these elements constitute components of an outer housing subassembly 17 that extends along an optical axis 18.

Figure 2:
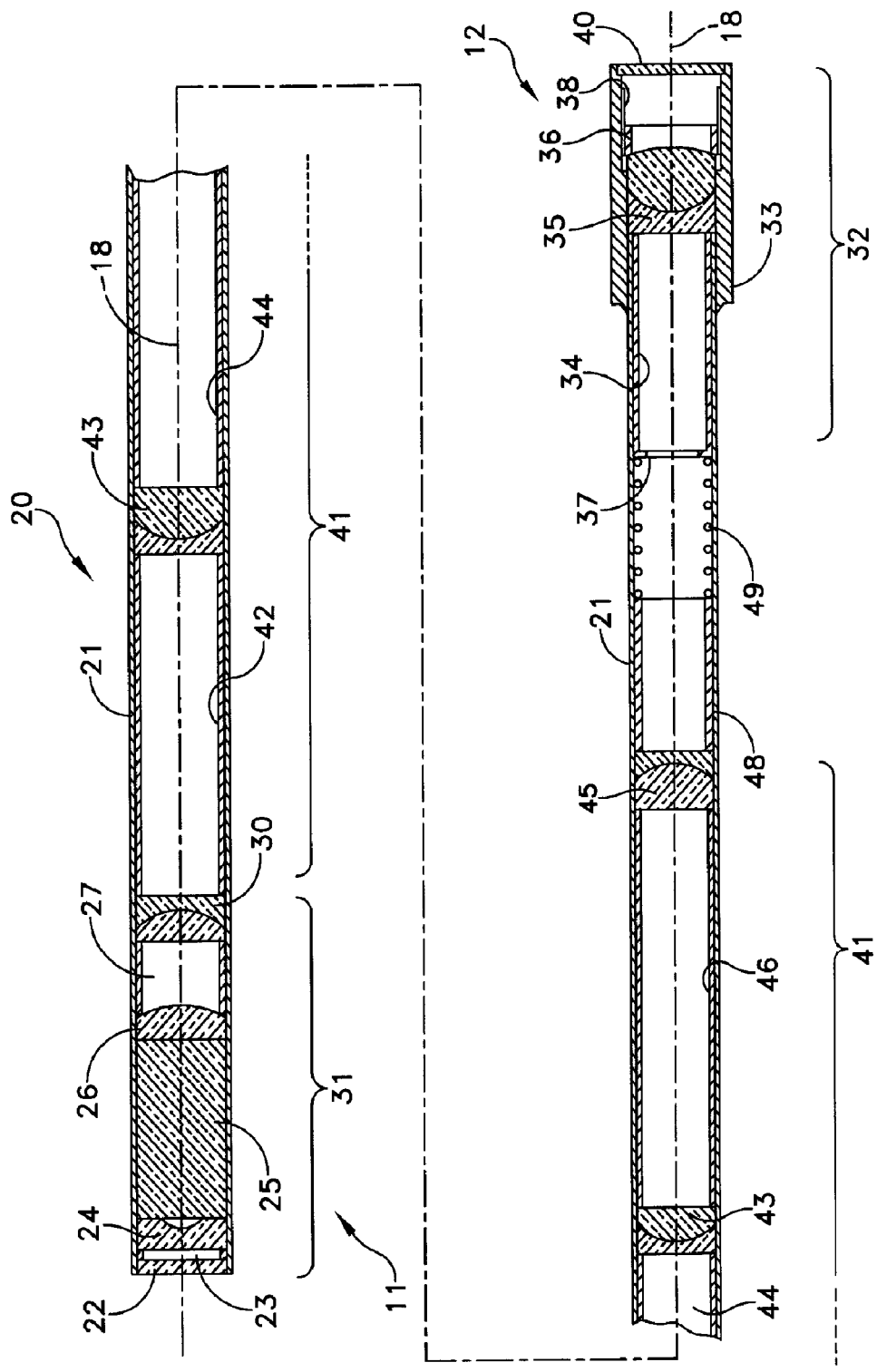
FIG. 2 provides a sectional view of the distal and proximal ends of an optics subassembly used in the endoscope of FIG. 1.

The endoscope 10 houses an optics subassembly 20 as shown in FIG. 2. Specifically the optics subassembly 20 includes a tubular sheath 21 that extends along the optical axis 18. A distal window 22 that is formed of any material that will withstand autoclaving temperatures, seals the tubular sheath 21 at the distal end 11. Sapphire windows are particularly suited. Brazing or soldering or other processes produce the seal between the distal window 22 and the tubular sheath 21. An annular spacer 23 can also be bonded to the interior of the tubular sheath 21 for further strength and to space a planoconcave lens 24 at an appropriate position along the optical axis 18.

The planoconcave lens 24, a rod lens 25, a planoconvex lens 26, a lens spacer 27 and an objective doublet lens 30 constitute an optical objective 31. As known, an optical objective 31 typically forms an image of an extended object lying perpendicular to the optical axis 18.

An eyepiece 32 at the proximal end 12 of the optics subassembly 20 extends into the tubular sheath 21 from the proximal end 12. The eyepiece 32 includes an axially extending collar 33 that is soldered or brazed to the tubular sheath 21.

Optical elements that form the eyepiece include an aperture/spacer 34, an eye lens 35 and a retainer 36. The aperture/spacer 34 spaces a reduced diameter field stop 37 at an appropriate distance from the eye lens 35. The retainer 36, that provides a positive end stop for the eyepiece elements, is externally threaded with internal threads 38 at the proximal end of the collar 33. A proximal window 40 seals the proximal end of the collar 33 like the distal window 22 seals the distal end of the tubular sheath 21.

A relay lens system 41 intermediate the optical objective 31 and the eyepiece 32 transfers an image from the optical objective 31 to the eyepiece 32, particularly to the field stop 37. A first spacer 42 positions a first relay doublet lens 43 relative to the objective doublet lens 30. Cylindrical intermediate lens spacers 44 and additional sets 43 of relay doublet lenses constitute additional optical elements that are spaced along the optical axis 18 in order to a proximal most relay doublet lens 45; that is, the relay doublet lens 45 closest to the proximal end 12. Generally the intermediate lens spacers 44 have the same configuration and length throughout the relay lens system. However, an end lens spacer 46 includes a field stop 47 and spaces the proximal most relay doublet lens 45 from an adjacent distally located relay lens doublet 43.

Still referring to FIG. 2, in this specific embodiment a sleeve spacer 48 abuts the distal side of the proximal most relay lens element 45; and a compression spring 49 lies between the sleeve spacer 48 and the aperture/spacer 34. The compression spring 49 acts to assure correct positioning of the optical elements in the tubular sheath 21 and to minimize stresses introduced by thermal expansion during autoclaving.

Figure 3:
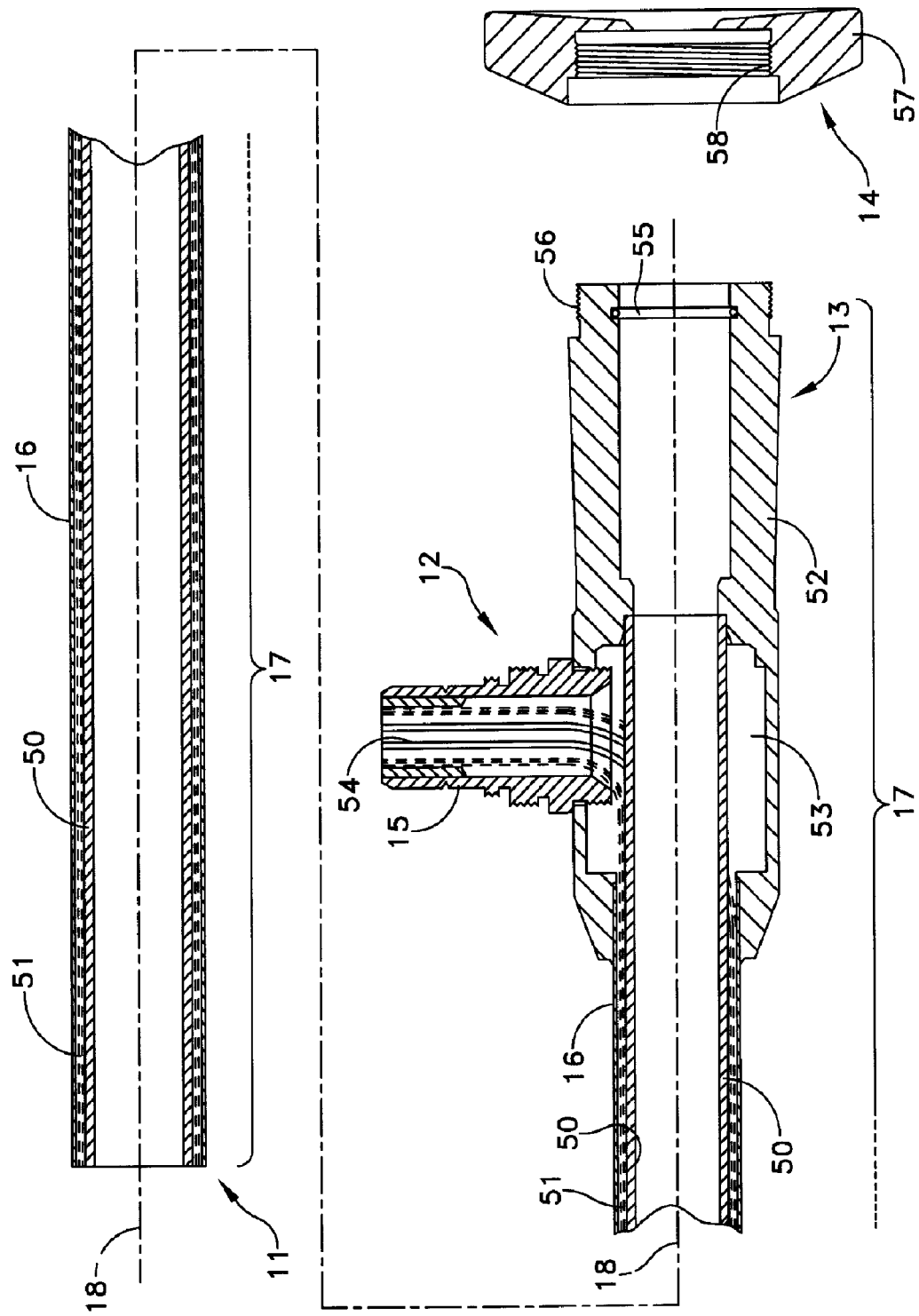
FIG. 3 provides a sectional view at the distal and proximal ends of an outer housing subassembly depicted in FIG. 1.

Now referring to FIG. 3, the outer tube 16 of the outer housing subassembly 17 is formed about a concentric, radially spaced inner tube 50 to form an annular space between the outer and inner tubes 16 and 50. Optical fiber 51 fills at least a portion, if not all, of the annular space to the distal end.

At the proximal end the outer tube 16 and inner tube 50 attach to a proximal body 52 that is shown as a one-piece device, but could be formed of multiple parts to adapt different components to a specific embodiment. A channel 53 allows the individual optical fibers 51 to be gathered into a cylindrical bundle 54 that terminates in the fiber post 15. The optical fibers 51 receive light delivered from an external source at the fiber post 15 and illuminate an object at the distal end 11.

The proximal body 52 terminates as its proximal end with an internal O-ring 55 and an externally threaded end portion 56 to receive the eyecup 14. The eyecup 14 includes a body portion 57 with internal threads 58. The use of eyecups with their attachment to structures, such as the proximal body 52, is well known in the art.

Figure 4:
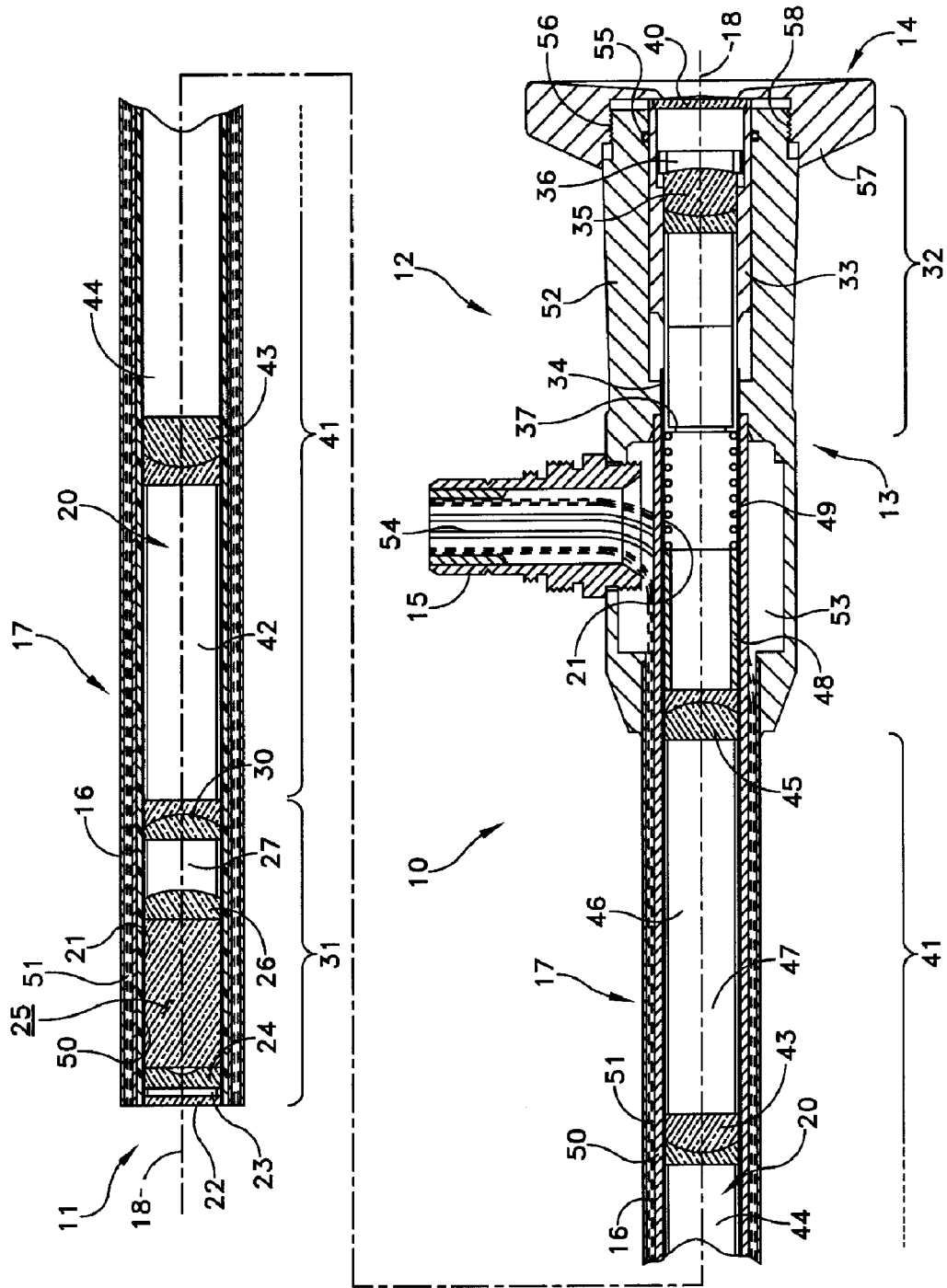
FIG. 4 provides a cross-sectional view at the distal and proximal ends of the assembled endoscope of FIG. 1.
Figure 4A:
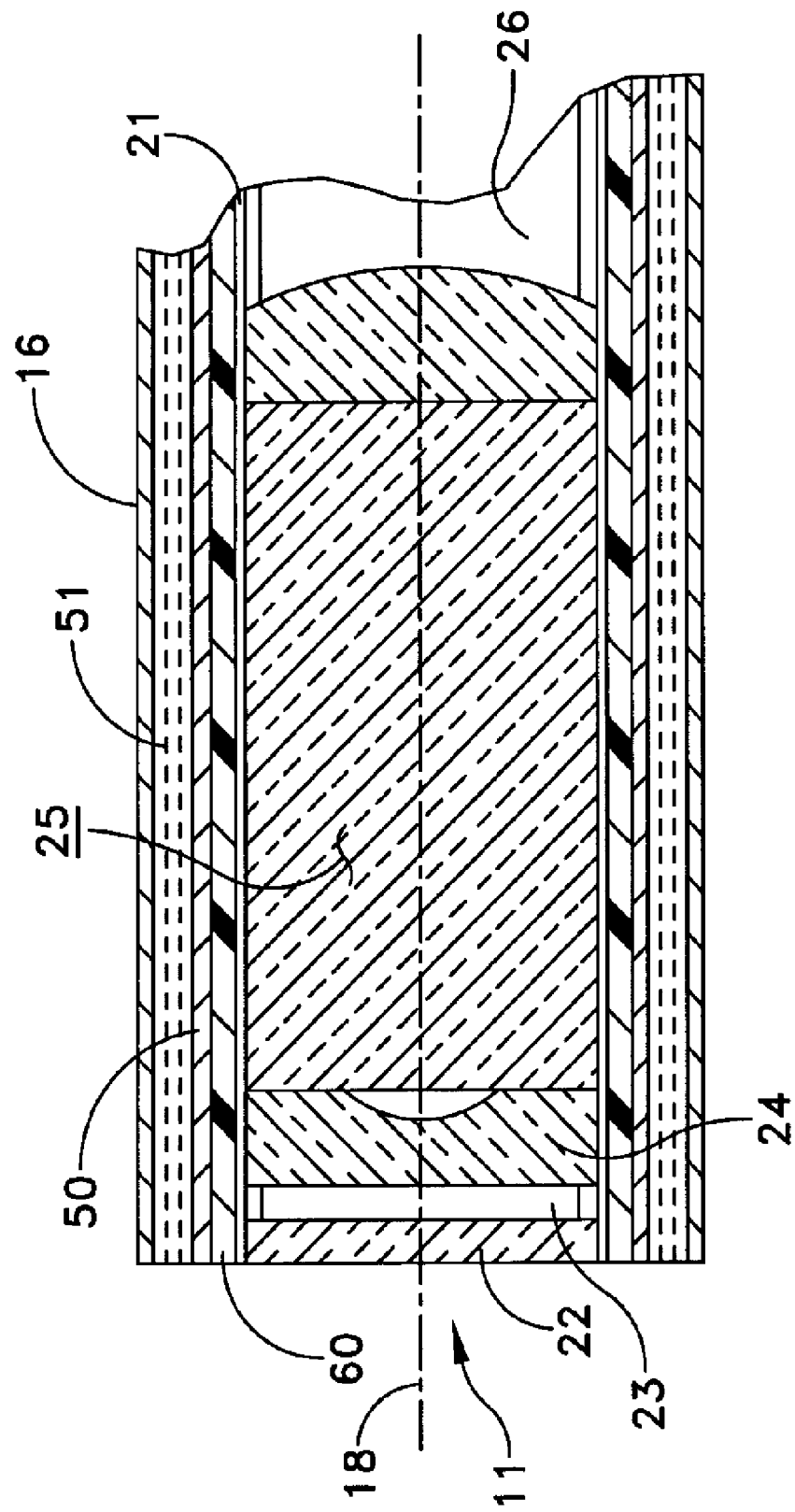
FIG. 4A is an enlarged cross-sectional view at the distal end.

Unlike prior art constructions, the endoscope 10 shown in FIGS. 4 and 4A contains no epoxy adhesive at the distal end to form a seal between the tubular sheath 21 and the inner tube 50. Rather an adhesive material 60 provides adhesion between the tubular sheath 21 and the inner tube 50 during normal use and yet allows adhesion to be overcome by the use of proper fixtures thereby to release the tubular sheath 21 from the inner tube 50.

In accordance with this invention, the adhesive material 60 has certain characteristics. The adhesive material 60 has a slow curing time thereby to allow the optics subassembly 20 to be properly positioned within the outer housing subassembly 17.

The adhesive material 60 also should be a Class VI material that is acceptable for use in medical devices. Class VI silicone adhesives constitute a general class of adhesives that are adapted for use in repairable endoscopes constructed in accordance with this invention.

For effecting repairability the adhesive material has an acceptable tear strength. The tear strength is determined by the axial extent of all the adhesive material 60 between the tubular sheath 21 and inner tube 50, the size of the gap and any limits imposed on an axial force that tries to withdraw the optics subassembly 20 from the outer housing subassembly 17. In addition the tear strength for the adhesive material will also be selected so that tearing of the adhesive will occur before any tension forces on the tubular sheath 21 exceed any yield stress levels. However, under normal use the adhesive material will not tear and thereby maintain the relative position of the optics subassembly 20 in the outer housing subassembly 17.

During manufacture the outer housing subassembly 17 shown in FIG. 3 is initially vertically oriented with the distal end 111 facing downward in a fixture that blocks the opening at the distal end 11. A predetermined quantity of the adhesive material 60 is then added into the passage defined by the inner tube 50. This may provide a bond over the entire length of the inner tube 50 or only a portion thereof depending upon the specific configuration of the endoscope. In any configuration the adhesive material will fill the gap beginning at the distal end 11.

Next the optics subassembly 20 of FIG. 2 is loaded into the outer housing subassembly 17 from the proximal end 12 along the axis 18 until the distal window 22 is at an appropriate position. Excess adhesive material is removed and the adhesive material is allowed to cure. After curing, the eyecup 14 is threaded onto the proximal body 52 until it abuts the proximal window 40 applying a force directed distally along the axis 18. This completes the manufacturing process except for quality control testing; the endoscope 10 is ready to use.

If damage occurs to either the outer housing subassembly 17 or the optics subassembly 20 of the endoscope 10 in FIG. 4, a repair operation begins by removing the eyecup 14, which may be sealed to the proximal body 52. A proximally directed force is then applied to the optics subassembly 20. One approach for producing this force is to push on the distal window 22 about its periphery until the adhesive material 60 "tears" and the optics subassembly 20 displaces within the outer housing subassembly 17. When this occurs the area at the proximal window 40 and adjoining portions of the collar 33 become available for attachment of a tool to fully withdraw the optics subassembly 20. In some applications the proximal window 40 and adjacent portions of the collar 33 extend beyond the proximal end of the proximal body portion 52 and afford an adequate surface for which tooling can be attached initially at the proximal end 12 for gripping and pulling the optics subassembly 20 from the outer housing subassembly 17. Conventional processes can be used to clean any residual adhesive material 60 from the inner tube 50. Then the repair can be made merely by replacing the damaged one of the outer housing subassembly 17 or the optics subassembly 20, inserting adhesive material and the optics subassembly 20 in the outer housing subassembly 17 by a procedure similar to that of the original manufacture. Consequently, this invention can be used to repair either a damaged outer housing subassembly or a damaged optics subassembly.

The walls of the tubular sheath 21 in some endoscopes become thin to reduce the overall diameter of the endoscope 10 for certain applications. With the structure in FIG. 4 it is possible to compress the tubular sheath 21 to the point that it warps. For example, as described earlier, after curing, the eyecup 14 is attached by being threaded onto the proximal body 52. Any rotation of the eyecup 14 after it abuts the proximal window 40 subjects the tubular sheath 21 to a compressive force because the tubular sheath 21 is held in place in the inner tube 50 by the adhesive material 60. If the eyecup 14 is over tightened, the tubular sheath 21 can warp whereby the lens elements are no longer coaxial and centered on the optical axis 18. Such warping can degrade a viewed image.

Figure 5:
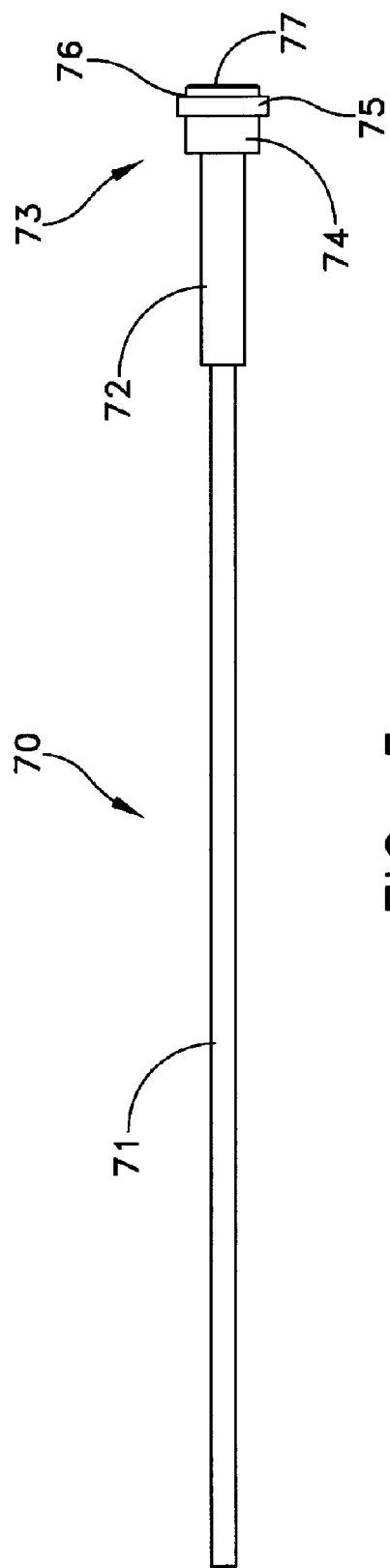
FIG. 5 is a plan view of an alternate optics subassembly for use in an endoscope.

FIGS. 5 through 8 describe an endoscope with a position stabilizer that accommodates such compressive forces without the potential for bending or warping a tubular sheath 71, such as shown in FIG. 5. The internal optical structure for the optics subassembly 70 is the same or equivalent to the optics subassembly 20. Consequently only the exterior of the sheath 71 and a collar 72 are disclosed in FIG. 5. Like the optics subassembly 20 in FIG. 2, the optics subassembly 70 includes a distal window (not shown) for sealing the distal end of the tubular sheath 71.

The collar 72 supports the proximal portion of the tubular sheath 71. At its proximal end the collar 72 carries a first positioning structure 73 including a distal shoulder 74, a circumferential and radially extending band 75 and a proximal shoulder 76. The proximal shoulder 76 circumscribes a proximal window 77. The proximal window 77 seals the optics subassembly 70 by being brazed or soldered to the proximal shoulder 76.

Figure 6:
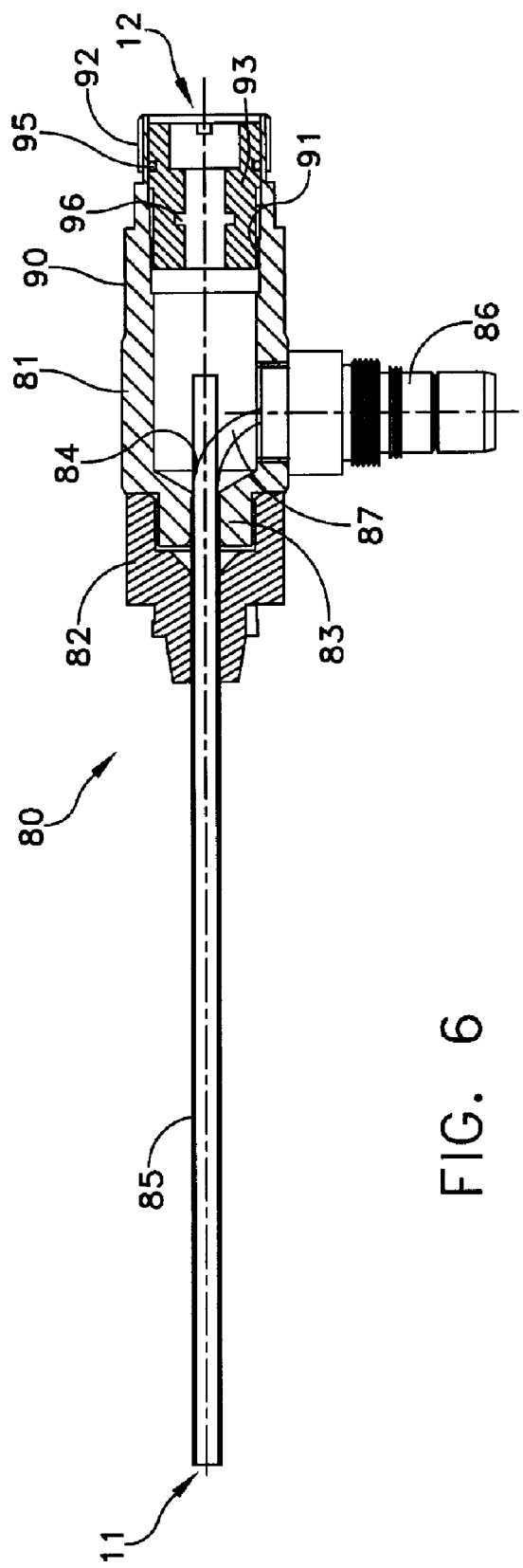
FIG. 6 is a sectional view of an alternative outer housing subassembly for receiving the optics subassembly of FIG. 5.
Figure 7:
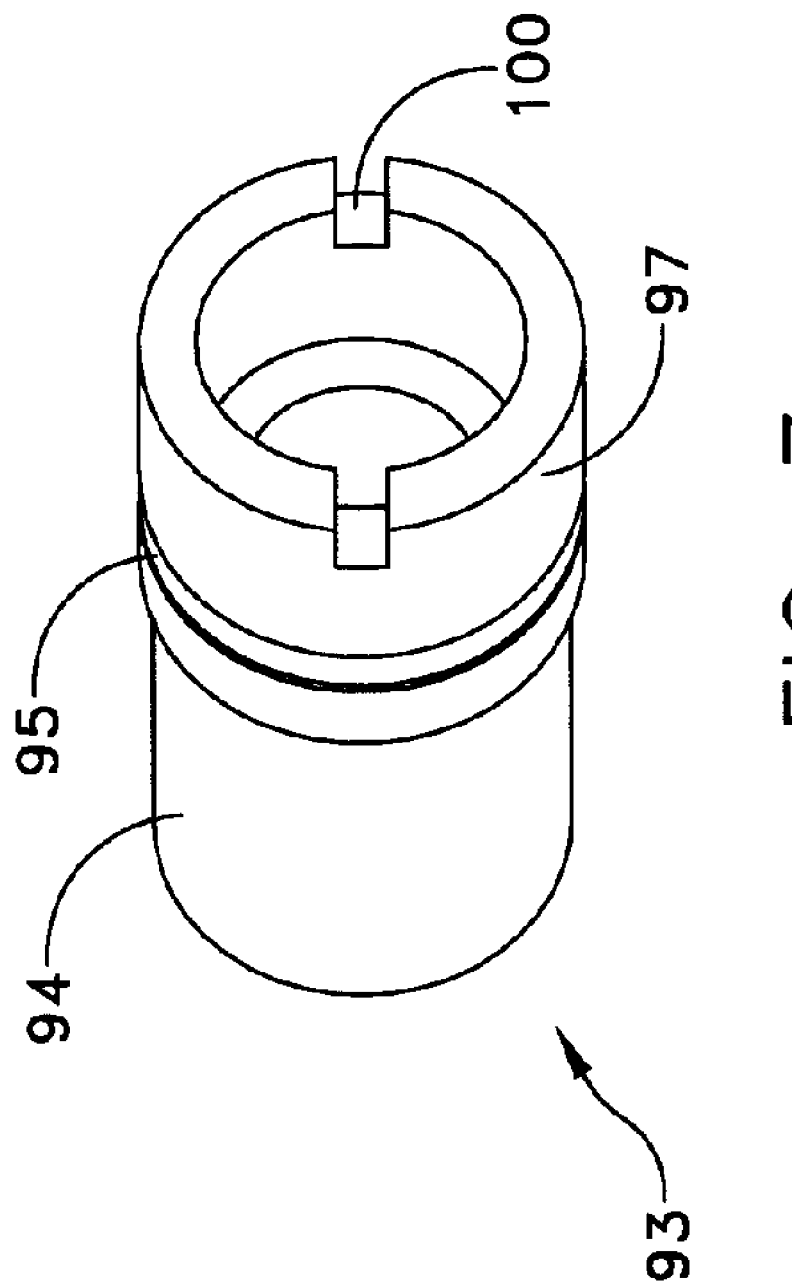
FIG. 7 is a perspective view of a positioner shown in the outer housing subassembly of FIG. 6.

FIGS. 6 and 7 depict an embodiment of an outer housing subassembly 80 that can receive the optics subassembly 70. As shown in FIG. 6, a proximal body 81 has an optional shroud adapter 82 attached to an end wall 83 with a central passage 84. The end wall 83 supports a double walled structure 85 within the proximal body 81. An optical fiber post 86 carries optical fibers 87 which then are routed through the annular space between the inner and outer walls to extend to distal end 11 of the double walled structure 85 in the same manner as the optical fiber 51 is gathered and routed through the annular space between the outer tube 16 and inner tube 50 in FIG. 4.

Still referring to FIG. 6, the proximal body 81 includes a proximal extension 90 with internal threads 91 and external threads 92. As shown in FIG. 6 and more clearly in FIG. 7, a second positioning structure 93 has external threads 94 for engaging the internal threads 91. The second positioning structure 93 includes an external O-ring channel 95 for providing an O-ring seal between the second positioning structure 93 and the proximal extension 90. The second positioning structure 93 also has an internal O-ring channel 95 for providing a seal when the optics subassembly 70 is inserted in the outer housing subassembly 80. A proximal extension 97 of the second positioning structure 93 has diametrically opposite proximal axial slots 100.

Figure 8:
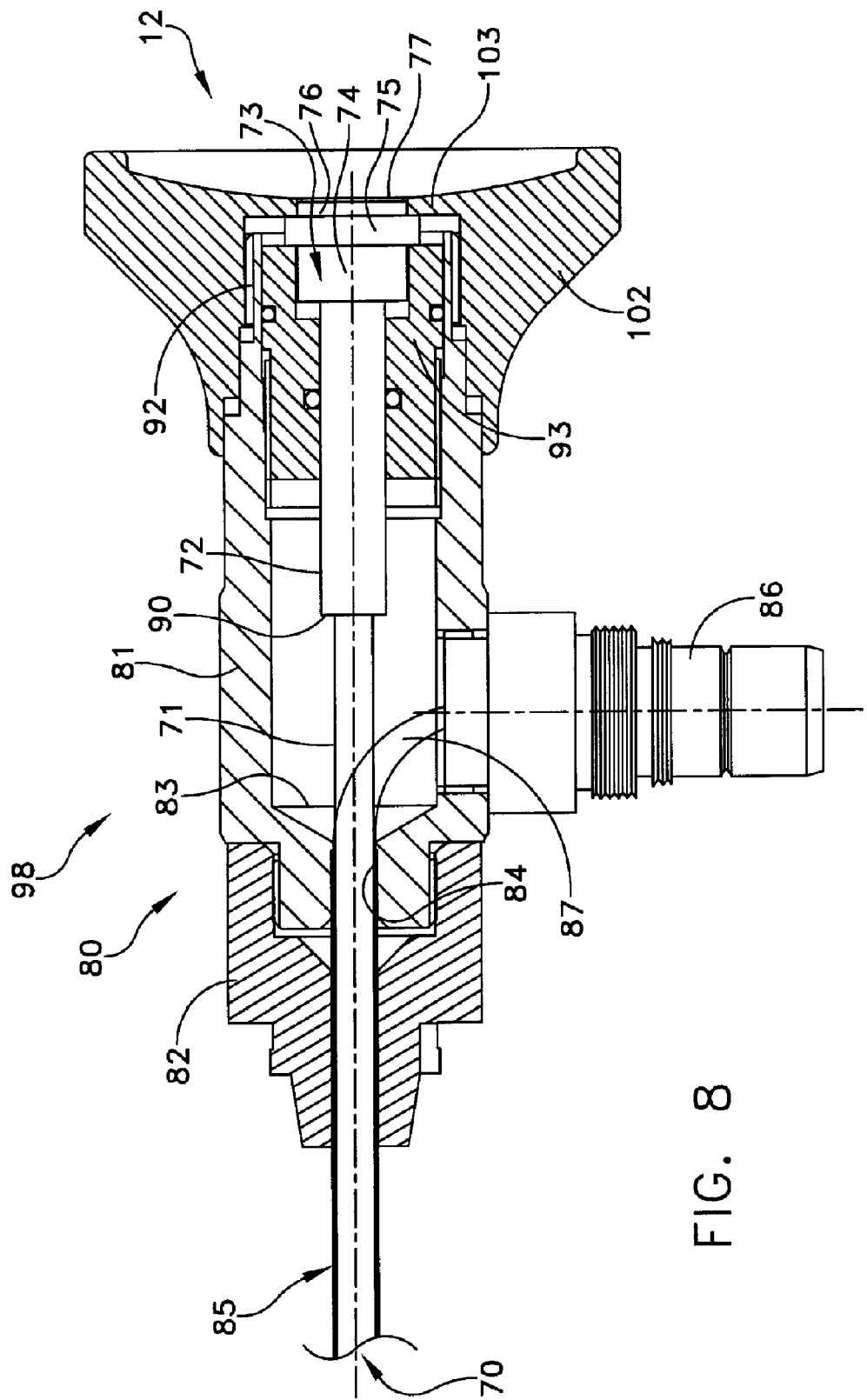
FIG. 8 is a sectional view of the proximal end of an endoscope with the subassemblies of FIGS. 5 and 6.

Referring to FIG. 8, during the construction of this particular embodiment of an endoscope 98, the outer housing subassembly 80 with the second positioning structure 93 removed will be positioned vertically in a fixture that blocks the open distal end 11. Then a predetermined amount of adhesive material will be introduced through the central passage 84 to fill the central lumen or passage of the double walled structure 85. Next the second positioning structure 93 will be threaded into the proximal body 81 thereby to constitute an adjustable stop that limits the distal position of the optics subassembly 70 in the outer housing subassembly 80. As a next step, the optics subassembly 70 is loaded into the outer housing subassembly 70 until the distal radial edge of the band 75 engages the proximal radial edge of the second positioning structure 93.

After removing any excess adhesive material, the eyecup 102 is threaded onto the external threads 92 until a central annular portion 103 engages the proximal radial edge of the band 75. Now the adhesive is allowed to cure. As will now be apparent, the band 75 absorbs all the compression forces. No significant compressive forces are translated to the tubular sheath 71 so any potential for damage due to compression of the tubular sheath 71 is essentially eliminated. At the distal end 11, the structure is analogous to the structure shown in FIG. 4A with the adhesive 60. In addition the second positioning structure 93 and the eyecup 102 stabilize the axial position of the optics subassembly 70 within the outer housing subassembly 80.

An endoscope has been constructed in accordance with this invention using the optics subassembly of FIG. 5 and the outer housing subassembly 80 of FIG. 6. Referring to both FIGS. 5 and 6, the double walled structure 85 has an outer diameter of 2.7 mm and a lumen of 2.2 mm. The sheath 71 has an outer diameter of 2.15 mm leaving a circumferential extending gap of 0.025 mm. A Class VI GE RTV 118 silicone is one example of a room temperature vulcanizing silicone. It has a tensile strength of about 2.20 MPa and a cure time of 12 to 24 hours and provides the characteristics needed to enable the repair of an endoscope in accordance with this invention when it extends through the lumen in the wall structure 85 from the distal end to the proximal end hereby being coincident with the length of the wall structure 85.

Should repairs be required, the eyecup 102 is removed. Then a tool can be inserted to engage proximal axial slots 100, shown in FIG. 7, in the end of the second positioning structure 93. The second positioning structure 93 can then be unthreaded thereby advancing proximally or to the right in FIG. 8. This applies a force in tension to the tubular sheath 71 until the adhesive material, like the adhesive material 60 in FIG. 4A, tears and releases any withholding force on the optics subassembly 70. Then the optics subassembly 70 can be removed for repair. After repair, the double wall passage receives new adhesive. The position of the second positioning structure 93 can be reset. Then a new or replacement optics subassembly can be reinserted in the outer housing subassembly 80 in a manner similar to that shown and described with respect to FIG. 4.

As will now be apparent, endoscopes, such as the endoscope 10 in FIGS. 1 through 4 or the endoscope 80 in FIGS. 5 through 8, constructed in accordance with this invention meet all the objectives of this invention. The optics subassemblies 20 and 70 are formed as sealed structures with solder or brazed seals at the proximal and distal ends that withstand repeated autoclaving.

The adhesive material between the optics subassembly and outer housing subassembly provides a gross seal that prevents any migration of bodily fluids during examination from the distal end of the endoscope into the proximal end where it might contact the physician. Migration of moisture past this seal does not affect the image because it does not enter the optics subassembly.

The use of an adhesive material by itself or in combination with a position stabilizer structure such as shown in FIGS. 5 through 8 provides a means for fixing the optics subassembly within the outer housing subassembly for normal use. However, this structure allows the removal of the optics subassembly merely by subjecting the optics subassembly to a removal force.

As described with respect to the manufacturing processes, it will be apparent that these objectives are met with a system that is simple and economical to assemble. Moreover and particularly with respect to the structure shown in FIGS. 5 through 8, this invention provides an endoscope which is adapted for thin-walled structures where compressive forces on an optics subassembly could have a deleterious effect.

Variations of the various components of the disclosed endoscopes have been discussed. Essentially FIGS. 1 through 4 and 5 through 8 depict two specific embodiments of an endoscope embodying this invention. Specific lens configurations and outline forms have been disclosed for acting as an objective, a relay and an eyepiece. Each of these could be modified while still attaining some or all of the benefits of this invention. It will be apparent that many other modifications could also be made to the disclosed apparatus without departing from the invention. Therefore, it is the intent of the appended claims to cover all such variations and modifications as come within the true spirit and scope of this invention.

What is claimed is:

1. A rigid endoscope having distal and proximal ends and being subject to a variety of forces in normal use comprising:
   A) a sealed rigid optics subassembly including an external sheath containing a distal window, an optical objective proximate said distal window, an eyepiece at a proximal end and relay lens system means for transferring an image from the optical objective to said eyepiece, B) a rigid outer housing subassembly including a passage with two open ends extending between the distal and proximal ends of said rigid endoscope whereby an annular gap exists between said optics subassembly and said outer housing subassembly, and C) adhesive material filling the gap for a distance from the distal end and adhering to the circumference of portions of said subassemblies thereby to position the distal ends to prevent displacement therebetween during normal use, said adhesive material having a tear strength that is greater than that required to withstand the forces encountered in normal use and that is less than any yield stress for said optics and outer housing subassemblies thereby to permit the separation of said subassemblies for repair without damage to said assemblies by the application of sufficient axially directed external forces to said subassemblies to exceed the tear strength whereby said subassemblies separate axially.

2. An endoscope as recited in claim 1 wherein said adhesive material comprises a slow-curing adhesive material.

3. An endoscope as recited in claim 1 wherein said adhesive material comprises a Class VI silicone adhesive material.

4. An endoscope as recited in claim 1 wherein said adhesive material comprises a Class VI room temperature vulcanizing silicone.

5. An endoscope as recited in claim 1 wherein said external sheath of said optics subassembly is sealed at both ends and carries optical elements whereby said endoscope is autoclavable.

6. An endoscope as recited in claim 5 wherein said adhesive material is coextensive with substantially the entirety of said external sheath.

7. An autoclavable rigid endoscope having distal and proximal ends and comprising:

A) a rigid outer housing subassembly having a central lumen extending between open ends at both the distal and proximal ends of said rigid endoscope, said outer housing subassembly including:
  i) spaced inner and outer concentric tubes that form an annular space therebetween, and
  ii) optical fiber within said annular space, B) a sealed rigid optics subassembly in said lumen including:
  i) a rigid tubular sheath having sealed windows at each of the distal and proximal ends and extending through the central lumen, said sheath being spaced from said inner tube thereby to form an annular gap therebetween,
  ii) a plurality of optical elements in said tubular sheath including an optical objective proximate the distal window, an eyepiece proximate the proximal window and relay lens system means for transferring an image of an object from said optical objective to the eyepiece thereby to present the image for viewing, and C) an adhesive material filling the annular gap intermediate said inner tube of said outer housing and said tubular sheath for a distance from the distal end and adhering to the circumference of portions of said subassemblies thereby to position the distal ends and to prevent displacement therebetween during normal use, said adhesive material having a tear strength that is greater than that required to withstand the forces encountered in normal use and that is less than any yield stress for said optics and outer housing subassemblies thereby to permit the separation of said optics subassembly from said outer housing subassembly by the application of sufficient external forces to said subassemblies to exceed the tear strength.

8. An autoclavable endoscope as recited in claim 7 wherein said adhesive material comprises a slow-curing adhesive material.

9. An autoclavable endoscope as recited in claim 7 wherein said adhesive material comprises a Class VI silicone material.

10. An autoclavable endoscope as recited in claim 7 wherein said adhesive material comprises a Class VI room temperature vulcanizing silicone.

11. An autoclavable endoscope as recited in claim 7 wherein said optics and outer housing subassemblies have first and second positioning structures, respectively and said endoscope includes means for fixing said positioning structures thereby to prevent significant compression loading on said tubular sheath.

12. An autoclavable endoscope as recited in claim 11 wherein said outer housing subassembly includes a proximal body with a proximal end opening and said second positioning structure includes adjustable positioning means for fixing the axial position of said optics subassembly in said outer housing subassembly.

* * * * *